(12) United States Patent
Peterson et al.

(10) Patent No.: US 10,520,025 B1
(45) Date of Patent: Dec. 31, 2019

(54) BEARING ASSEMBLY FOR USE IN AXIAL-FLOW CARDIOPULMONARY BYPASS BLOOD PUMPS AND RELATED PUMPS

(71) Applicant: US Synthetic Corporation, Orem, UT (US)

(72) Inventors: S. Barrett Peterson, Orem, UT (US); Michael A. Vail, Genola, UT (US)

(73) Assignee: US Synthetic Corporation, Orem, UT (US)

( * ) Notice: Subject to any disclaimer, the term of this patent is extended or adjusted under 35 U.S.C. 154(b) by 553 days.

(21) Appl. No.: 13/761,944

(22) Filed: Feb. 7, 2013

Related U.S. Application Data

(60) Provisional application No. 61/599,728, filed on Feb. 16, 2012.

(51) Int. Cl.
| | | |
|---|---|---|
| *A61M 1/36* | (2006.01) | |
| *A61M 1/10* | (2006.01) | |
| *F16C 33/04* | (2006.01) | |
| *A61M 1/12* | (2006.01) | |

(52) U.S. Cl.
CPC ........... *F16C 33/043* (2013.01); *A61M 1/101* (2013.01); *A61M 1/122* (2014.02); *A61M 1/3666* (2013.01)

(58) Field of Classification Search
CPC ...... A61M 1/10; A61M 1/101; A61M 1/1015; A61M 1/1046; A61M 1/122; A61M 1/1017; A61M 1/1031; F04D 1/00; F04D 25/026; F04D 29/0476; F04D 3/00
USPC ...................................................... 604/4.01
See application file for complete search history.

(56) References Cited

U.S. PATENT DOCUMENTS

| | | | | |
|---|---|---|---|---|
| 4,789,251 A | * | 12/1988 | McPherson | F16C 17/04 384/317 |
| 5,613,935 A | * | 3/1997 | Jarvik | A61M 1/1018 600/16 |
| 5,965,089 A | * | 10/1999 | Jarvik | A61M 1/101 422/44 |
| 6,210,133 B1 | * | 4/2001 | Aboul-Hosn | A61M 1/101 417/423.1 |
| 6,793,681 B1 | * | 9/2004 | Pope | A61F 2/30767 623/22.11 |
| 7,635,035 B1 | | 12/2009 | Bertagnolli et al. | |
| 7,866,418 B2 | | 1/2011 | Bertagnolli et al. | |
| 7,870,913 B1 | * | 1/2011 | Sexton et al. | 175/107 |
| 8,236,074 B1 | | 8/2012 | Bertagnolli et al. | |

(Continued)

OTHER PUBLICATIONS

U.S. Appl. No. 61/599,728, filed Feb. 16, 2012, Peterson et al.

(Continued)

*Primary Examiner* — Ariana Zimbouski
(74) *Attorney, Agent, or Firm* — Dorsey & Whitney LLP

(57) ABSTRACT

Embodiments of the invention relate to bearing assemblies and associated cardiopulmonary bypass blood pumps in which the bearing assembly includes a stator and a rotor each including bearing surfaces oriented so as to be generally opposed to one another. The bearing surface may comprise a polycrystalline diamond material including a plurality of bonded diamond grains defining a plurality of interstitial regions therebetween, in which a non-metallic catalyst (e.g., a carbonate) and/or at least one derivative thereof is disposed interstitially between the bonded diamond grains.

27 Claims, 11 Drawing Sheets

(56) References Cited

U.S. PATENT DOCUMENTS

| | | | |
|---|---|---|---|
| 8,641,594 B2* | 2/2014 | LaRose | A61M 1/101 600/16 |
| 2008/0085407 A1* | 4/2008 | Cooley et al. | 428/336 |
| 2008/0269880 A1* | 10/2008 | Jarvik | 623/3.13 |
| 2010/0084196 A1* | 4/2010 | Bertagnolli | C22C 26/00 175/428 |
| 2010/0212971 A1* | 8/2010 | Mukhopadhyay | C22C 26/00 175/428 |
| 2010/0242375 A1* | 9/2010 | Hall et al. | 51/307 |
| 2012/0241224 A1 | 9/2012 | Qian et al. | |

OTHER PUBLICATIONS

U.S. Appl. No. 12/185,457, filed Aug. 4, 2008, Vail et al.
U.S. Appl. No. 12/495,986, filed Jul. 1, 2009, Bertagnolli et al.
De Somer et al. "Blood Pumps in Cardiopulmonary Bypass", Cardiopulmonary Bypass: Principles and Practice, 2nd edition, Edited by Glenn P. Gravlee, M.D., Richard F. Davis, M.D., Sep. 4, 2007.
John, "Current Axial-Flow Devices—the HeartMate II and Jarvik 2000 Left Ventricular Assist Devices", Semin Thoracic and Cardiovascular Surgery 20, pp. 264-272 (2008).
Reul et al., "Blood pumps for circulatory support", Perfusion 200; 15, pp. 295-311 (2000).

\* cited by examiner

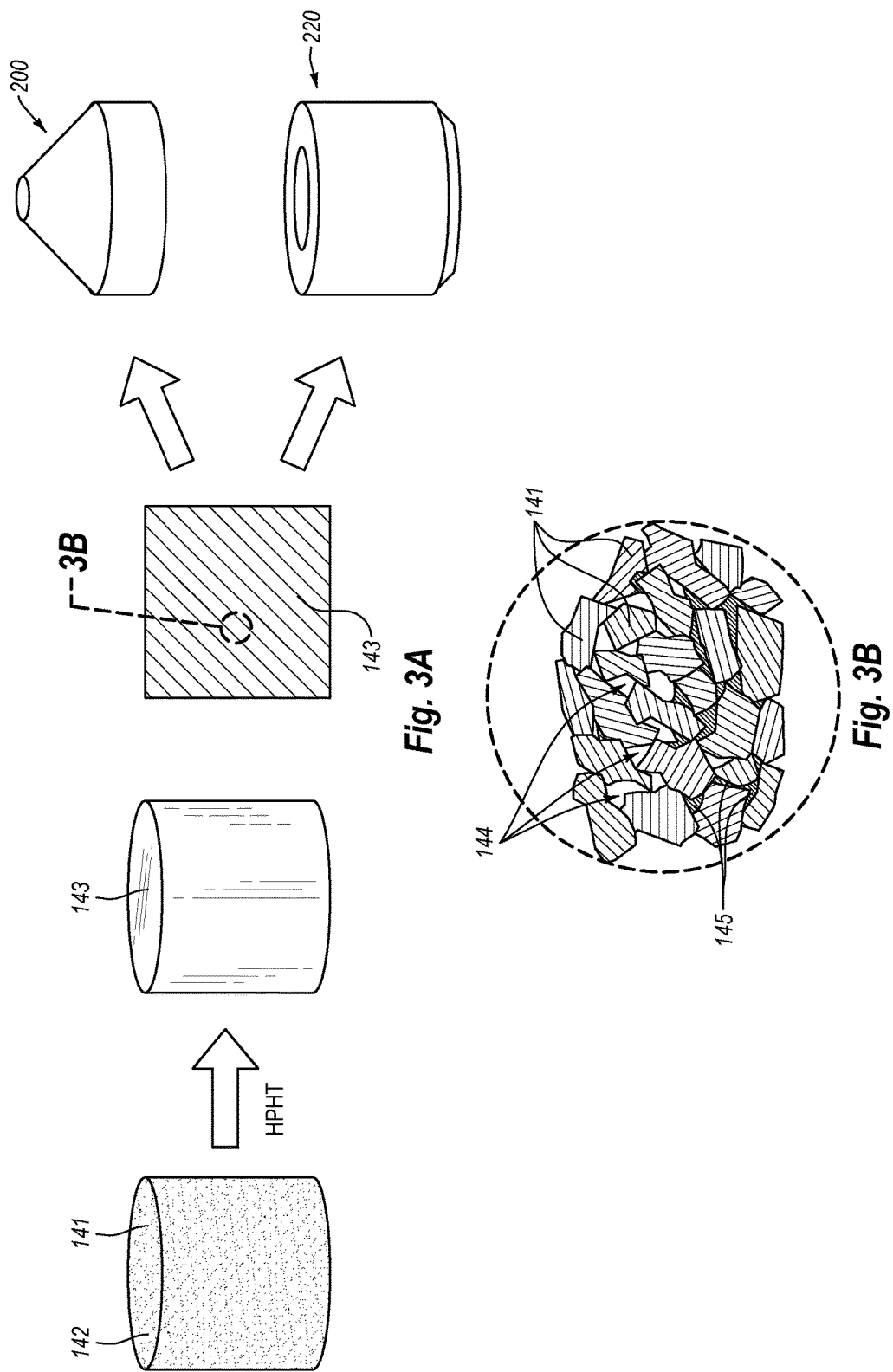

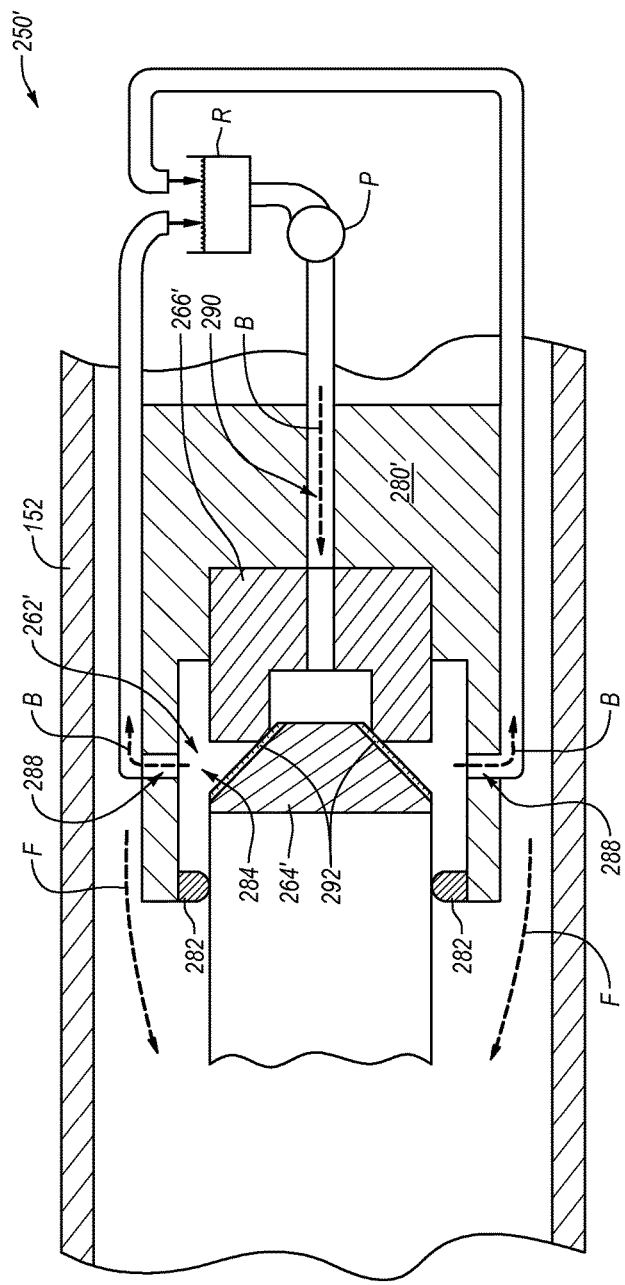
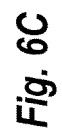
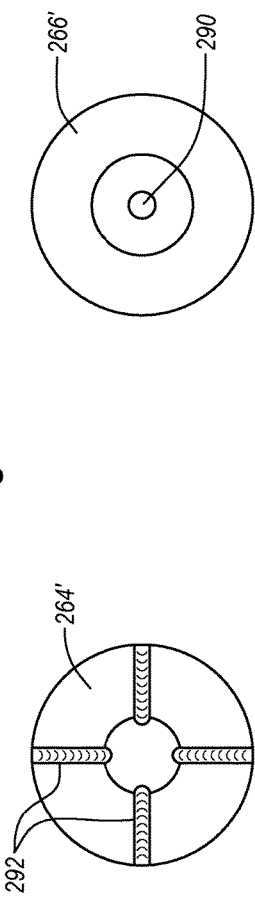
Fig. 6A
Fig. 6B
Fig. 6C

BEARING ASSEMBLY FOR USE IN AXIAL-FLOW CARDIOPULMONARY BYPASS BLOOD PUMPS AND RELATED PUMPS

CROSS-REFERENCE TO RELATED APPLICATIONS

This application claims priority to U.S. Provisional Application No. 61/599,728 filed on 16 Feb. 2012, the contents of which are incorporated herein, in their entirety, by this reference.

BACKGROUND

Mechanical cardiac assist pump devices have increasingly been used to maintain blood circulation and supply oxygen to organs and body tissue during a cardiopulmonary bypass procedure or where the natural heart is otherwise incapable of functioning as desired.

Such cardiopulmonary bypass pumps are typically centrifugal or roller (i.e., peristaltic) pump designs. Such designs provide advantages of simplicity of operation, reliability, and relatively low cost. One particular disadvantage of roller pump designs is blood damage (e.g., red blood cell damage and platelet activation) that can occur, and particulate spallation, a condition in which particulates from the tubing or pump components break off, contaminating the blood. As a result, the use of roller pumps can be generally limited to no more than about 4 hours.

Centrifugal pumps have increasingly been used as blood pumps. Such centrifugal pumps tend to exhibit lower incidence of blood damage, absence of spallation, and their use may be extended for periods of up to several days, if needed. However, the size of both roller pump and centrifugal pump configurations tend to be fairly large.

Therefore, manufacturers and users of blood pumps continue to seek improved blood pumps.

SUMMARY

Embodiments of the invention relate to polycrystalline diamond ("PCD") bearing assemblies for use in axial-flow cardiopulmonary bypass pumps and associated axial-flow cardiopulmonary bypass pumps that employ such PCD bearing assemblies. An embodiment of a bearing assembly includes a bearing stator and a bearing rotor. The stator and rotor each comprise a PCD element, and each PCD element includes an associated bearing surface, with the bearing surfaces of the stator and rotor oriented so as to be generally opposed to one another. In an embodiment, the PCD element of the rotor is shaped to have a generally conical portion, with the PCD element of the opposed stator being complementary configured to receive the generally conical bearing portion of the associated rotor. In an embodiment, the complementary shaped stator may include an inverted generally conically shaped portion. In other embodiments, various other shaped configurations for the rotor and stator may be employed.

Each PCD rotor and stator element includes a plurality of bonded diamond grains defining a plurality of interstitial regions therebetween. Typical PCD elements may be formed in a high-pressure/high-temperature ("HPHT") process in which a volume of diamond particles is placed with a metal-solvent catalyst (e.g., typically cobalt or nickel) into a container or cartridge. The metal-solvent catalyst may be provided in the form of a metal-solvent catalyst-cemented carbide (e.g., cobalt cemented tungsten carbide) substrate to which a PCD element is to be bonded. When a substrate is employed, the substrate and volume of diamond particles are processed under HPHT conditions in the presence of the metal-solvent catalyst that causes the diamond particles to bond to one another to form a matrix of bonded diamond grains defining a PCD element.

The cobalt or other metal-solvent catalyst (e.g., present as a cementing constituent in the substrate) liquefies and sweeps from a region adjacent to the volume of diamond particles into interstitial regions between the diamond particles during the HPHT process. The metal-solvent catalyst acts to promote intergrowth between the diamond particles, which results in the formation of a matrix of bonded diamond grains having diamond-to-diamond bonding therebetween, with interstitial regions between the bonded diamond grains being occupied by the metal-solvent catalyst.

While it is possible to leach the metal-solvent catalyst from the resulting PCD element (e.g., through exposure to a suitable acid), there remains some fraction of residual metal-solvent catalyst within interstitial regions of the PCD element, even after such a leaching procedure. A different catalyst is employed in PCD elements used in bearing assemblies and associated blood pumps according to embodiments of the invention. The inventors have found that non-metallic catalysts of, for example carbonate materials, particularly alkali metal and/or alkaline earth metal carbonates, may be used to catalyze the desired intergrowth between diamond particles. The PCD element includes a non-metallic catalyst and/or at least one derivative thereof (e.g., rather than cobalt or nickel) disposed within at least some of the interstitial regions of the PCD element. Of course, most or even substantially all of the non-metallic catalyst and/or at least one derivative thereof may be subsequently removed through leaching or other suitable process, although some portion of the non-metallic catalyst and/or derivative thereof will typically be present interstitially.

In addition to carbonate catalysts, hydroxide catalysts (e.g., alkali metal and/or alkaline earth metal hydroxides) may also be suitable for use. One such suitable hydroxide may include magnesium hydroxide. Other non-metallic catalysts that may be suitable for use include phosphorus, sulfur, or combinations thereof. Another contemplated non-traditional catalyst that may be suitable for use is copper or copper alloys.

In an embodiment, an axial-flow blood pump for use in cardiopulmonary bypass treatment may comprise a housing including an inlet at an inlet end, an outlet at an outlet end, and a longitudinal axis extending generally therebetween. The axial-flow blood pump further includes a rotatable shaft disposed within the housing between the inlet and outlet, the shaft including at least one blade on an exterior surface thereof configured to direct blood entering the housing through the inlet towards the outlet. The pump includes a motor (e.g., any suitable motor such as an electromagnetic motor) configured to rotate the shaft about a longitudinal axis thereof, an inlet bearing assembly disposed at the inlet end of the rotatable shaft, and an outlet bearing assembly disposed at the outlet end of the rotatable shaft. Each bearing assembly includes a stator and a rotor, each of which comprises a PCD element in which at least some of the interstitial regions between diamond grains of the PCD element are occupied by a non-metallic catalyst and/or at least one derivative thereof.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

FIG. 3A is a schematic illustration of an embodiment of a method for fabricating PCD bearing elements such as those shown in FIGS. 1A-2D.

FIG. 3B is a schematic illustration of the microstructure of the PCD body from which the PCD bearing element fabricated according to the method of FIG. 3A may be made according to an embodiment.

FIG. 6A is a schematic cross-sectional view of another embodiment of a substantially sealed PCD bearing assembly that also includes a central through passageway in the stator and a plurality of grooves in a surface of the rotor.

FIG. 6B is a end elevation view of the rotor of the bearing assembly shown in FIG. 6A.

FIG. 6C is a end elevation view of the stator of the bearing assembly shown in FIG. 6A.

DETAILED DESCRIPTION

Embodiments of the invention relate to bearing assemblies comprising PCD elements that are particularly configured for use in applications where the PCD bearing elements contact blood, for example, as bearing assemblies in an axial-flow cardiopulmonary bypass blood pump. Such bearing assemblies may include a rotor and a stator, each of which includes bearing surfaces oriented generally opposed to one another, and in which the bearing surfaces are formed of a PCD element including a plurality of bonded diamond grains defining a plurality of interstitial regions therebetween. Rather than employing a metal-solvent catalyst (e.g., cobalt or nickel) to sinter the diamond grains together into a PCD structure, a non-metallic catalyst may be employed, for example, such as a carbonate catalyst. An alkali metal carbonate, an alkaline earth metal carbonate (e.g., magnesium carbonate), or combinations thereof may be employed as the non-metallic catalyst. Such non-metallic catalyst may be substantially free of cobalt, substantially free of nickel, and substantially free of iron.

When exposed to HPHT conditions, one theory is that the magnesium carbonate or other suitable carbonate catalyst donates the carbon of the carbonate, which may be transformed to diamond during the sintering process, while the remaining constituents of the carbonate molecule may be at least partially or substantially completely converted to an oxide of the alkali or alkaline earth element (e.g., magnesium oxide). The oxide may be present within at least some of the interstitial regions of the resulting PCD structure, which oxide is a derivative of the carbonate catalyst material. Further, the presence of such an oxide may be generally acceptable from a biocompatibility perspective. The resulting PCD element including the bearing surface of each rotor and stator is substantially free of cobalt and nickel. The PCD element may also be free of iron.

In addition to carbonate catalysts, hydroxide catalysts (e.g., alkali metal and/or alkaline earth metal hydroxides) may also be suitable for use. One such suitable hydroxide catalyst may include magnesium hydroxide. Other non-metallic catalysts that may be suitable for use include phosphorus, sulfur, or combinations thereof. Another contemplated non-traditional catalyst that may be suitable for use is copper and copper alloys. While copper and copper alloys are, of course, traditionally considered a metal or alloy, they may be generally acceptable from a biocompatibility perspective.

The term "non-metallic" encompasses, and may be used to describe carbonates and hydroxides of alkali and alkaline earth metals. By way of clarification, such compounds are not considered "metals" within the scope of that term as used herein. This is so even though the carbonate or hydroxide compounds may include one or more metal atoms, because the metal atoms are not present in a native metal form.

Figure 1A:
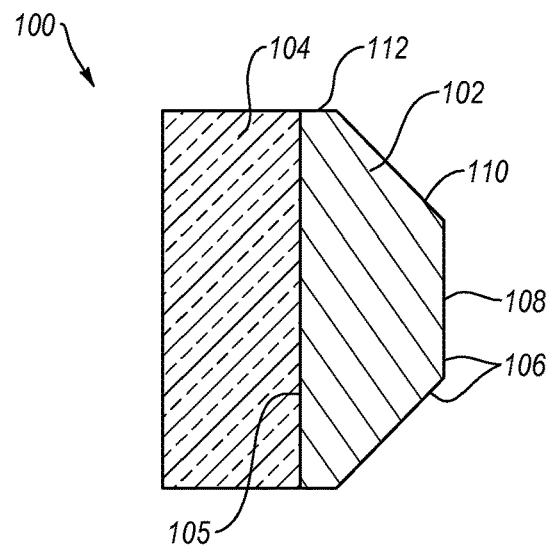
FIG. 1A is a cross-sectional view of an embodiment of a rotor including a PCD element.

FIG. 1A is a cross-sectional view of an embodiment of a bearing rotor 100 including a PCD element 102 that is bonded to substrate 104. Substrate 104 may be any suitable carbide material, for example, tungsten carbide. In another embodiment, substrate 104 may be a medical-grade biocompatible metallic material, such as titanium, a cobalt-chromium alloy (e.g., Co—Cr—Mo), or another biomedically acceptable material or alloy. PCD rotor element 102 includes an exterior surface 106, which includes a distal surface 108, a tapered, bearing surface 110, and a lateral surface 112. Tapered bearing surface 110 may be tapered (e.g., generally conical) towards distal surface 108, so as to have a diameter or thickness adjacent lateral surface 112 that is greater than a diameter or thickness of bearing surface 110 at distal surface 108, as shown. In an embodiment, not all of exterior surface 106 may bear against an opposed bearing surface of a stator during use. Rather, the portions of exterior surface 106 that actually bear against an opposed stator bearing surface may depend on the configuration of the opposed stator. For example, distal surface 108, lateral surface 112, or both may or may not actually contact or bear against an opposed bearing surface of the stator, as will be apparent from FIG. 1C. In addition, a portion of tapered bearing surface 110 may not contact or bear against an opposed stator bearing surface.

Figure 1B:
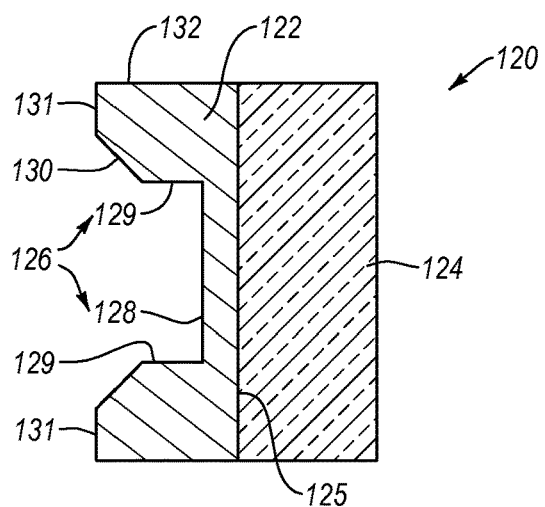
FIG. 1B is a cross-sectional view of an embodiment of a stator including a PCD element shaped to be complementary with the rotor of FIG. 1A.

FIG. 1B is a cross-sectional view of an embodiment of a bearing stator 120 that may include a PCD element 122 which is bonded to carbide substrate 124. PCD element 122 also includes an exterior surface 126, which is configured to complement at least part of tapered bearing surface 110 of rotor 100. For example, exterior surface 126 may include a proximal surface 128, a tapered or chamfered bearing surface 130, and a lateral surface 132. Depending on the particular configuration of bearing surface 130, a distal surface 131 may also be present. In an embodiment, bearing surface 130 may resemble a portion of a generally inverted cone, so as to be shaped to receive and bear against a generally conical bearing surface 110 of rotor 100. In other embodiments, bearing surfaces 110 and 130 may be generally spherical or shaped as otherwise desired. In an embodiment, the bearing surface 130 only includes a single bearing surface as shown, for example, in FIG. 3A. The cavity defined by proximal surface 128 and side surfaces 129 may be generally cylindrical (e.g., where PCD stator element 120 is generally circular in cross-section), and distal surface 131 may appear as an annular rim disposed around the perimeter of PCD stator element 120.

Figure 1C:
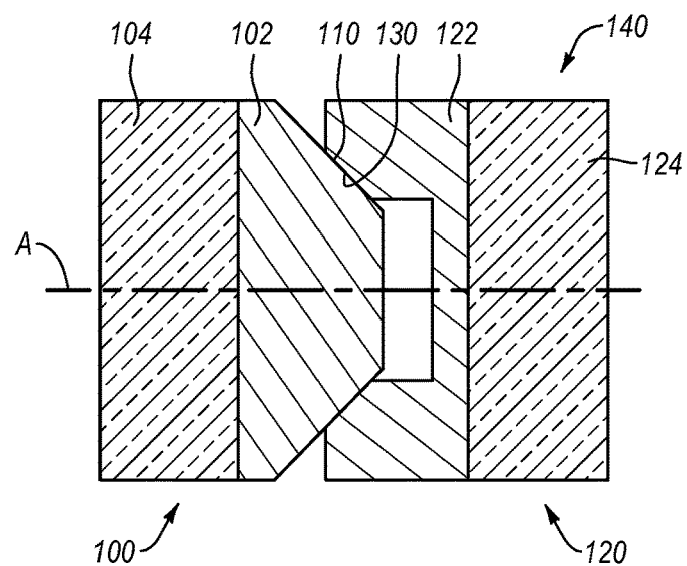
FIG. 1C is a cross-sectional view of a bearing assembly including the rotor and stator of FIGS. 1A and 1B.
Figure 1D:
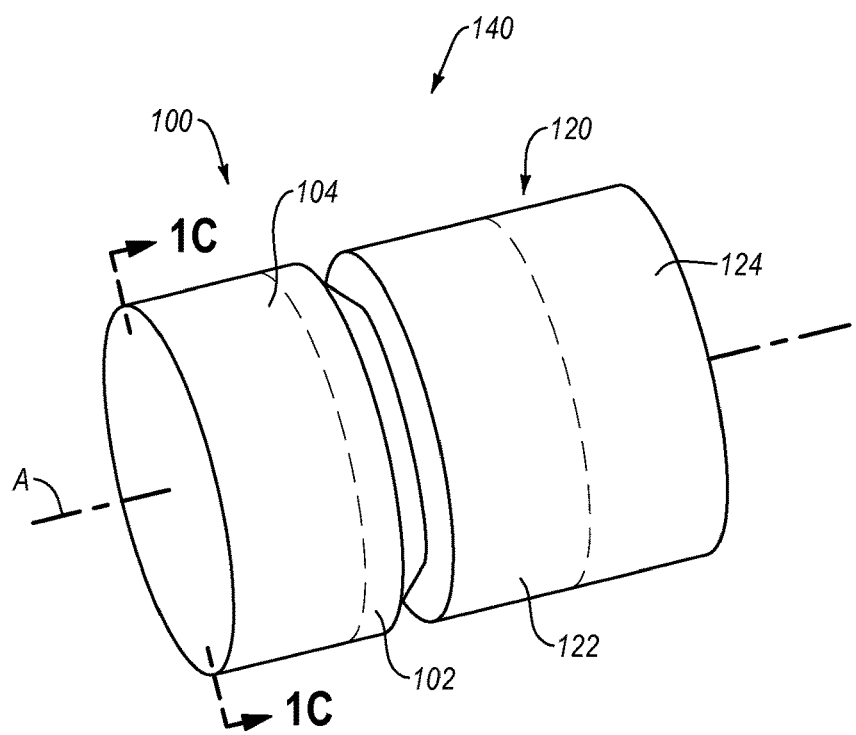
FIG. 1D is an isometric view of the bearing assembly of FIG. 1C.

FIG. 1C illustrates the rotor 100 and stator 120 positioned adjacent to one another, as during use and in which the bearing surface 110 of rotor 100 is oriented to bear against opposed bearing surface 130 of stator 120. FIG. 1D is an isometric view of this assembled orientation. As shown, in an embodiment, the bearing surfaces are not generally perpendicular to the longitudinal axis A of bearing assembly 140, but may be offset from perpendicular as a result of the generally tapered shape of bearing surface 110 and generally inverted tapered shape of bearing surface 130. In an embodiment, the angle between longitudinal axis A and bearing surfaces 110, 130 may be between about 30° and about 60° (e.g., about 45°).

FIGS. 2A-2D show an alternative bearing assembly configuration in which the rotor and stator do not include a carbide substrate, but in which the rotor and stator components are formed substantially entirely from PCD. Such configurations that do not include a carbide substrate may be advantageous in eliminating bonding difficulties between PCD and a substrate. In addition, such configurations may further improve the biocompatibility of the bearing assembly. For example, a carbide substrate such as substrates 104 and 124 of bearing assembly 140 may often be cemented carbide materials including carbide particles cemented with cobalt, nickel, or both. It may also be difficult to bond a substrate to PCD bearing surfaces that are substantially free of cobalt, nickel, and iron and thus a configuration that does not include such a cemented carbide substrate may be particularly advantageous.

Figure 2A:
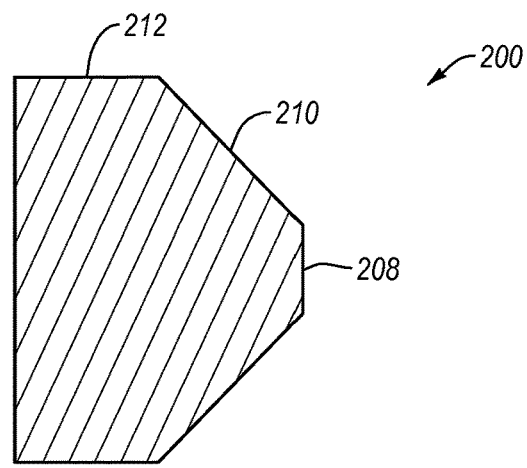
FIG. 2A is a cross-sectional view of another embodiment of a rotor including a PCD element.
Figure 2B:
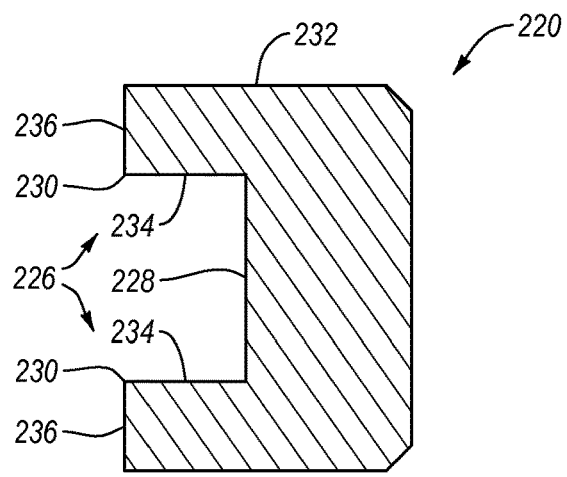
FIG. 2B is a cross-sectional view of another embodiment of a stator including a PCD element shaped to be complementary with the rotor of FIG. 2A.

The shape of both the rotor and stator of FIGS. 2A-2D are also shown as somewhat different from the shapes shown in FIGS. 1A-1D. The rotor 200 shown in FIG. 2A, is similar in shape to rotor 100 of FIG. 1A, but distal surface 208 has been reduced (e.g., reduced in surface area), while the length of tapered generally conical bearing surface 210 has been increased. In addition, entire rotor 200 may comprise a PCD material. Lateral surface 212 may have a height approximately equal to the combined thickness of lateral surface 112 and substrate 104 of rotor 100. It will be understood that other shaped embodiments are also possible. In addition, in an embodiment, the shape of the rotor and stator may be as that shown in FIGS. 1A-1D, but the entire rotor and stator (i.e., including carbide portions 104 and 124) may be formed of the PCD material. In another embodiment, the shapes of the rotor and stator may be as that shown in FIGS. 2A-2D, but in which the proximal portion of each of the rotor and stator is formed of a carbide substrate, while the distal portion of each is formed of PCD that is bonded to the substrate.

The shape of stator 220 is also generally similar to that of stator 120 (e.g., having a cross-section that is generally U-shaped). However, instead of a bearing surface, stator 220, as perhaps best seen in FIG. 2C, includes a bearing edge 230 defined between the intersection of side surfaces 234 with distal surface 236. In another embodiment, a chamfer may be provided between surfaces 234 and 236, which would form a generally inverted conical bearing surface for bearing against bearing surface 210 of rotor 200. Providing such a chamfer may help prevent or minimize chipping of the stator 220 where the bearing surfaces contact one another. Selecting a bearing surface area may provide for a desired frictional resistance between surfaces of rotor 200 and stator 220 during operation.

Figure 2C:
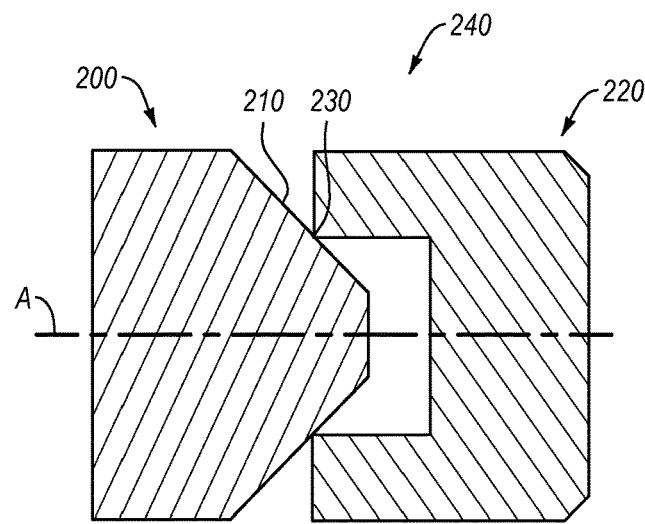
FIG. 2C is a cross-sectional view of another bearing assembly including the rotor and stator of FIGS. 2A and 2B.
Figure 2D:
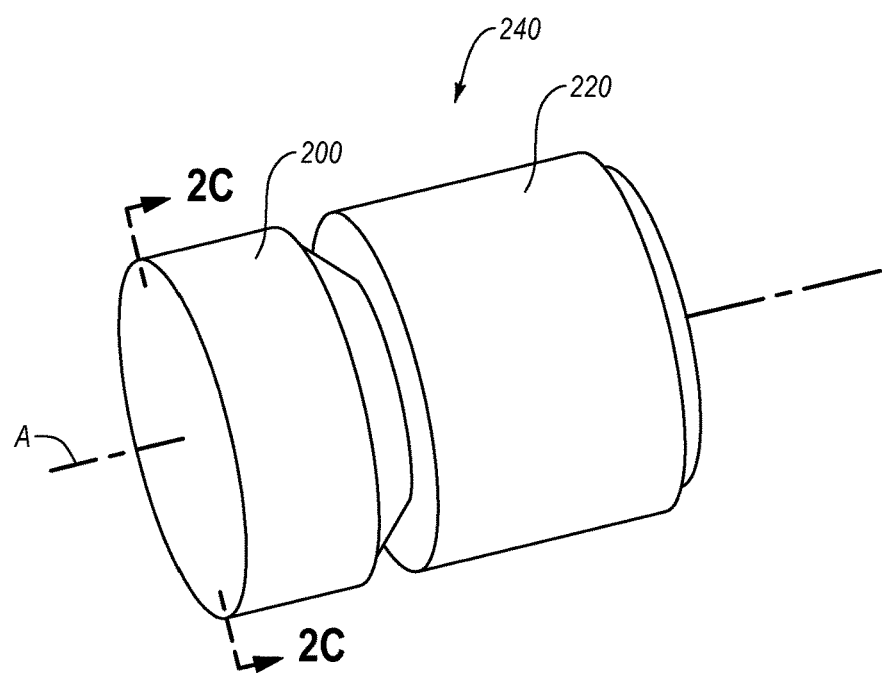
FIG. 2D is an isometric view of the bearing assembly of FIG. 2C.

Although not specifically illustrated, another embodiment may be the converse of that shown in FIG. 2C where the stator includes a bearing surface (rather than rotor 200 including bearing surface 210) and the rotor includes a bearing edge (rather than stator 220 including bearing edge 230).

Various other bearing assembly configurations including a PCD rotor and a PCD stator may be employed. Generally, an embodiment may include a rotor and/or stator with a generally conically shaped portion, at least a portion of which serves as a bearing surface, and which is oriented to be generally opposed to a corresponding bearing surface and/or bearing edge of the stator and/or rotor, respectively, during use. While specific configurations of stators and rotors are shown in the Figures, it will be understood that the rotating elements and the stationary elements may be interchanged in contemplated alternative embodiments.

In any case, the PCD bearing surfaces include a carbonate catalyst and/or derivative thereof disposed within at least some of the interstitial regions defined between bonded diamond grains of the PCD element. Use of a carbonate catalyst rather than traditionally employed metal-solvent catalysts, such as cobalt or nickel, may be advantageous for operation of the bearing at high speeds, increased temperatures, for certain material properties, or combinations of the foregoing. In addition, it may be suitable with respect to biocompatibility issues.

If the rotor, stator, or both include a carbide substrate, such substrates may include, without limitation, cemented carbides, such as tungsten carbide, titanium carbide, chromium carbide, niobium carbide, tantalum carbide, vanadium carbide, or combinations thereof cemented with iron, nickel, cobalt, or alloys thereof. In an embodiment, any optional substrate (e.g., 104 and/or 124) included as a component of the rotor or the stator comprises tungsten carbide. When present, in some embodiments, the carbide may be cemented with iron or an iron alloy, rather than cobalt or nickel. Although the interfacial surface 105, 125 of the PCD elements 100, 120 is depicted in FIGS. 1A-1C as being substantially planar, in other embodiments, the interfacial surface 105, 125 may exhibit a selected non-planar topography.

The PCD element (e.g., 102, 122, 200, 220) includes a plurality of directly bonded-together diamond grains having diamond-to-diamond bonding (e.g., $sp^3$ bonding) therebetween. The plurality of bonded diamond grains define a plurality of interstitial regions. Although not employing a non-metallic carbonate catalyst, it may be possible to employ PCD elements that are cobalt-sintered structures that are subsequently leached to remove the interstitial cobalt from the PCD element. Various example processes for fabricating such PCD elements sintered with cobalt or another metal are disclosed in U.S. Pat. No. 7,866,418 and U.S. patent application Ser. No. 11/545,929, each of which is herein incorporated by reference in its entirety by this reference. That said, in an embodiment, the interstitial regions of the PCD element may include a carbonate catalyst and/or derivative thereof disposed therein. While at least some of the interstitial regions are occupied by the carbonate catalyst and/or derivative thereof, most or even substantially all of the catalyst and/or derivative thereof may be leached or otherwise removed from the PCD element. Even if leaching is performed, a small fraction of the carbonate catalyst and/or derivative thereof typically remains present within at least some of the interstitial regions of the PCD element. Where the catalyst or catalyst derivative is leached out, the interstitial regions may be backfilled with another (or the same) material by an infiltration process, if desired.

Metal-solvent catalysts such as cobalt are often leached out of the PCD material by exposing the exterior surface of the PDC element to an acid, such as aqua regia, nitric acid, hydrochloric acid, hydrofluoric acid, or mixtures thereof. Such an acid leaching process may be suitable for removal of some carbonate catalysts and/or derivatives thereof. In another embodiment, the carbonate catalyst and/or derivative thereof may be removed by vacuum evaporation or another suitable technique. Even after removal, a residual, identifiable amount of the carbonate catalyst and/or derivative thereof may remain in at least some of the interstitial regions of the PCD element.

The carbonate catalyst used in sintering the diamond particles into a PCD element for the bearing assembly may be selected from alkali metal or alkaline earth metal carbonates. Examples of alkali metal carbonates include, but are not limited to, carbonates of Li, Na, K, or combinations thereof. Examples of alkaline earth metal carbonates include, but are not limited to, Be, Mg, Ca, Sr, Ba, or combinations thereof. A combination of both alkali and alkaline earth carbonates may also be employed.

As shown in FIG. 3A, the PCD elements of any of the bearing assemblies may be fabricated by subjecting a plurality of diamond particles 141 to an HPHT sintering process in the presence of the carbonate catalyst (e.g., magnesium carbonate) 142 to facilitate intergrowth between the diamond particles 141 and form a PCD body 143 comprised of bonded diamond grains that exhibit diamond-to-diamond bonding therebetween. For example, the carbonate catalyst 142 may be mixed with the diamond particles 141 or infiltrated from a carbonate catalyst disc, wafer, or powder adjacent to the diamond particles 141.

As mentioned previously, the diamond particle size distribution of the plurality of diamond particles 141 may exhibit a single mode, or may be a bimodal or greater grain size distribution. In an embodiment, the diamond particles 141 may comprise a relatively larger size and at least one relatively smaller size. The one or more selected sizes may be determined, for example, by passing the diamond particles through one or more sizing sieves or by any other method. As used herein, the phrases "relatively larger" and "relatively smaller" refer to particle sizes (by any suitable method) that differ by at least a factor of two (e.g., 30 µm and 15 µm). According to various embodiments, the diamond particles may include a portion exhibiting a relatively larger average particle size (e.g., 50 µm, 40 µm, 30 µm, 20 µm, 15 µm, 12 µm, 10 µm, 8 µm) and another portion exhibiting at least one relatively smaller average particle size (e.g., 6 µm, 5 µm, 4 µm, 3 µm, 2 µm, 1 µm, 0.5 µm, less than 0.5 µm, 0.1 µm, less than 0.1 µm). In an embodiment, the diamond particles 141 may include a portion exhibiting a relatively larger average particle size between about 10 µm and about 40 µm and another portion exhibiting a relatively smaller average particle size between about 1 µm and 4 µm. In some embodiments, the diamond particles 141 may comprise three or more different average particle sizes (e.g., one relatively larger average particle size and two or more relatively smaller average particle sizes), without limitation.

The plurality of diamond particles 141 including carbonate catalyst 142 may be placed in a pressure transmitting medium, such as a refractory metal can embedded in pyrophyllite or other pressure transmitting medium. The pressure transmitting medium, including the plurality of diamond particles 141 and the carbonate catalyst 142 may be subjected to an HPHT process using an ultra-high pressure press (e.g., a cubic press) to create temperature and pressure conditions at which diamond is stable. The temperature of the HPHT process may be at least about 1000° C. (e.g., about 1200° C. to about 2000° C.) and the pressure of the HPHT process may be at least 4.0 GPa (e.g., about 5.0 GPa to about 8.0 GPa) for a time sufficient for the plurality of diamond particles to be sintered together. The carbonate catalyst 142 is capable of wetting and/or reacting with the diamond particles 141 and the carbonate catalyst 142 and/or at least one derivative thereof becomes positioned within the interstitial regions 144 between the bonded diamond particles of the resulting PCD body 143. For example, the temperature of the HPHT process may be at least about 1000° C. (e.g., about 1200° C. to about 2000° C.) and the pressure of the HPHT process may be at least 5.0 GPa cell pressure (e.g., at least about 7 GPa, about 7.5 GPa to about 12.0 GPa cell pressure, about 7.5 GPa to about 9.0 GPa cell pressure, or about 8.0 GPa to about 10.0 GPa cell pressure) for a time sufficient to sinter the diamond particles 141 to form the PCD body 143. In an embodiment, the pressure of the HPHT process may be about 5 GPa to about 7 GPa and the temperature of the HPHT process may be about 1150° C. to about 1400° C. (e.g., about 1200° C. to about 2000° C.).

In an embodiment, the carbonate catalyst 142 may comprise a mixture of alkali metal carbonates. For example, according to one embodiment, the carbonate catalyst may comprise lithium carbonate, sodium carbonate, and potassium carbonate present in selected proportions at or near a ternary eutectic composition (e.g., a eutectic composition, a hypereutectic composition, or a hypoeutectic composition) for the lithium carbonate-sodium carbonate-potassium carbonate chemical system. In the lithium carbonate-sodium carbonate-potassium carbonate chemical system, the ternary eutectic composition occurs when the lithium carbonate is present in an amount of about 43.5 atomic percent, the sodium carbonate is present in an amount of about 31.5 atomic percent, and the potassium carbonate is present in an amount about 25 atomic percent and the ternary eutectic melts at a temperature of about 397° C. at standard pressure. At elevated pressures, the melting temperature is higher. Such a carbonate catalyst mixture may be HPHT processed between about 1100° C. to about 2000° C. at approximately 7.7 GPa cell pressure. Additional details of carbonate catalyst compositions that may be employed are disclosed in U.S. patent application Ser. No. 12/185,457, U.S. patent application Ser. No. 12/495,986, and U.S. patent application Ser. No. 13/070,636 the disclosure of each of which is incorporated herein, in its entirety, by this reference.

When the carbonate catalyst includes one or more alkaline earth metal carbonates (e.g., magnesium carbonate), the temperature of the HPHT process may be significantly higher, for example between about 1900° C. to about 2200° C. and a cell pressure of between about 6 to about 8 GPa.

Without being bound by theory, it is believed that the carbonate catalyst may be partially or substantially completely converted to one or more corresponding alkali metal and/or alkaline earth oxides during the HPHT sintering process, such that it is the alkali metal or alkaline earth metal oxide, which is a derivative of the alkali metal or alkaline earth metal carbonate, that is interstitially present in the PCD body 143 after HPHT processing. Any residual carbonate may be partially or substantially completely converted to an oxide by heat treatment of the PCD body 143. For example, the PCD body 143 may be heated in air, argon, nitrogen, or partial vacuum at a temperature of about 800° C. to about 1400° C. to partially or substantially completely convert residual carbonates to corresponding oxides. Additional details of catalysts that do not include cobalt or nickel, and that may be suitable for use in embodiments of the invention are disclosed in U.S. patent application Ser. No. 12/495,986 and U.S. Pat. No. 7,635,035, the disclosures of each of which are incorporated herein, in their entirety, by this reference.

Upon sintering, the bonded diamond particles include interstitial regions 144 defined therebetween, with the carbonate catalyst and/or at least one derivative thereof 145 (FIG. 3B) disposed within the interstitial regions 144 (FIG. 3B). The as-sintered PCD body 143 may be leached by immersion in an acid or subjected to another suitable process such as vacuum evaporation to remove at least a portion of the carbonate catalyst or derivative thereof 145 from the interstitial regions 144 of the PCD body 143. For example, the as-sintered PCD body 143 may be immersed in an acid for about 2 to about 7 days (e.g., about 3, 5, or 7 days) or for a few weeks (e.g., about 4 weeks) depending on the process employed. In another embodiment, at least a portion of carbonate catalyst and/or derivative thereof 145 may be removed through vacuum evaporation (e.g., by heating the PCD body 143 under a partial vacuum until a desired amount of the carbonate catalyst and/or derivative thereof evaporates). Various other leaching or removal processes may be employed, such as using a leaching agent (e.g., a liquid, a gas, or combinations thereof) at elevated temperature, elevated pressure, or both.

Even after acid leaching or removal of the carbonate catalyst or derivative thereof by another technique, a residual amount of carbonate catalyst or derivative thereof may typically remain in some of the interstitial regions between the bonded diamond grains of the PCD body. Such residual interstitial material may be identifiable using mass spectroscopy, energy dispersive x-ray spectroscopy microanalysis, or other suitable analytical technique. It may be possible to reduce the concentration of such carbonate catalyst and/or derivative thereof to less than about 10% by weight, less than about 5% by weight, less than about 3% by weight, or less than about 1% by weight. Such entrapped, residual carbonate catalyst or derivative thereof may be difficult to remove, even with extended removal treatment times.

The PCD body 143 may be formed during sintering to have any initial shape. A cylindrical shape is one typical configuration resulting after sintering. As-sintered shapes other than cylinders may also be possible including sintering the PCD body 143 substantially to net shape so that no or minimal post sintering shaping is required. Such a cylindrically shaped PCD body 143 may subsequently be subjected to at least one shaping process to achieve the desired rotor configuration 200 or stator configuration 220. Such shaping may be accomplished through electro-discharge machining (where a sufficient concentration of metal catalyst is present), laser cutting, grinding, lapping, other method, or combinations thereof to achieve the desired geometry. If the carbonate catalyst or derivative thereof is to be removed, this may be performed either before or after shaping, as desired.

Figure 4A:
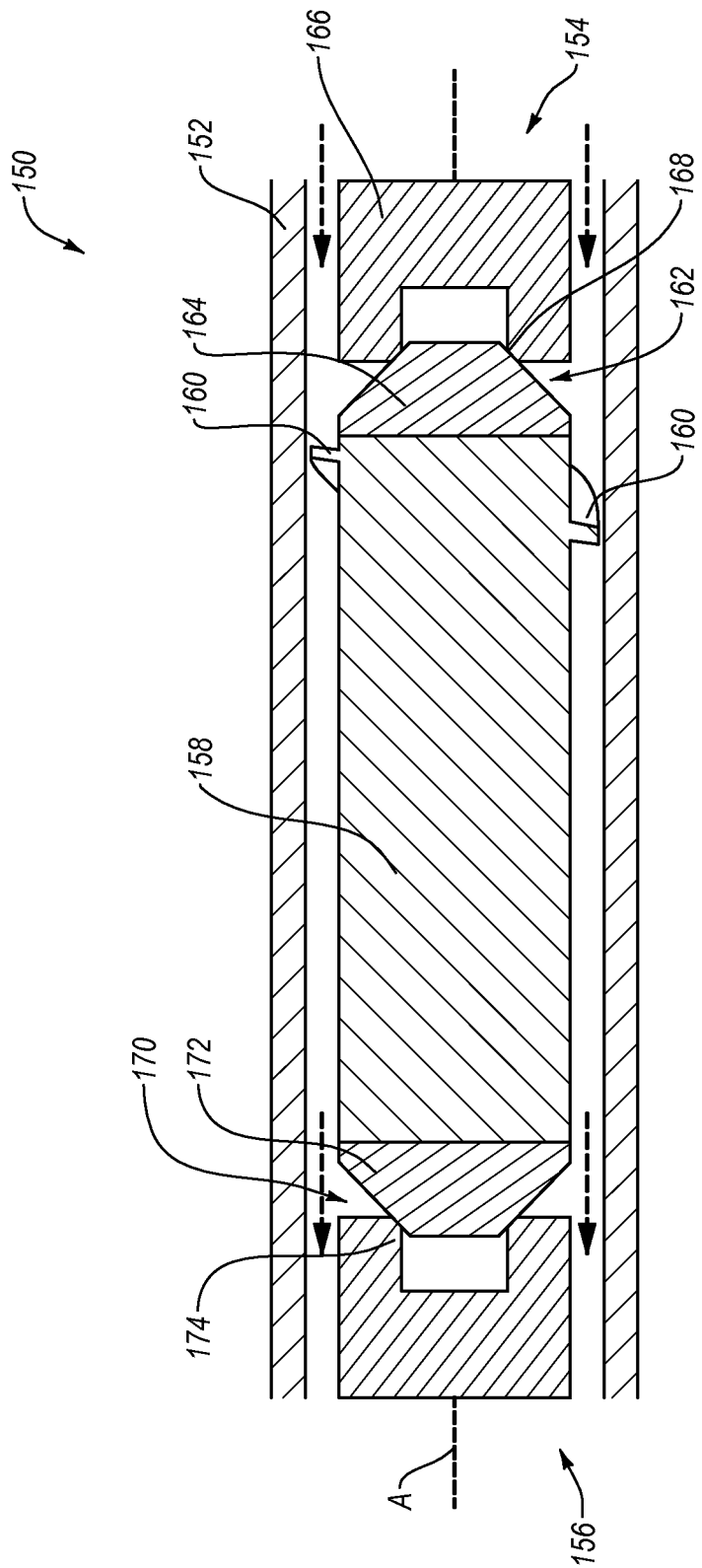
FIG. 4A is a cross-sectional view of an embodiment of an axial-flow blood pump including a housing, a rotatable shaft, an inlet, an outlet, and PCD bearing assemblies on either end of the rotatable shaft.
Figure 4B:
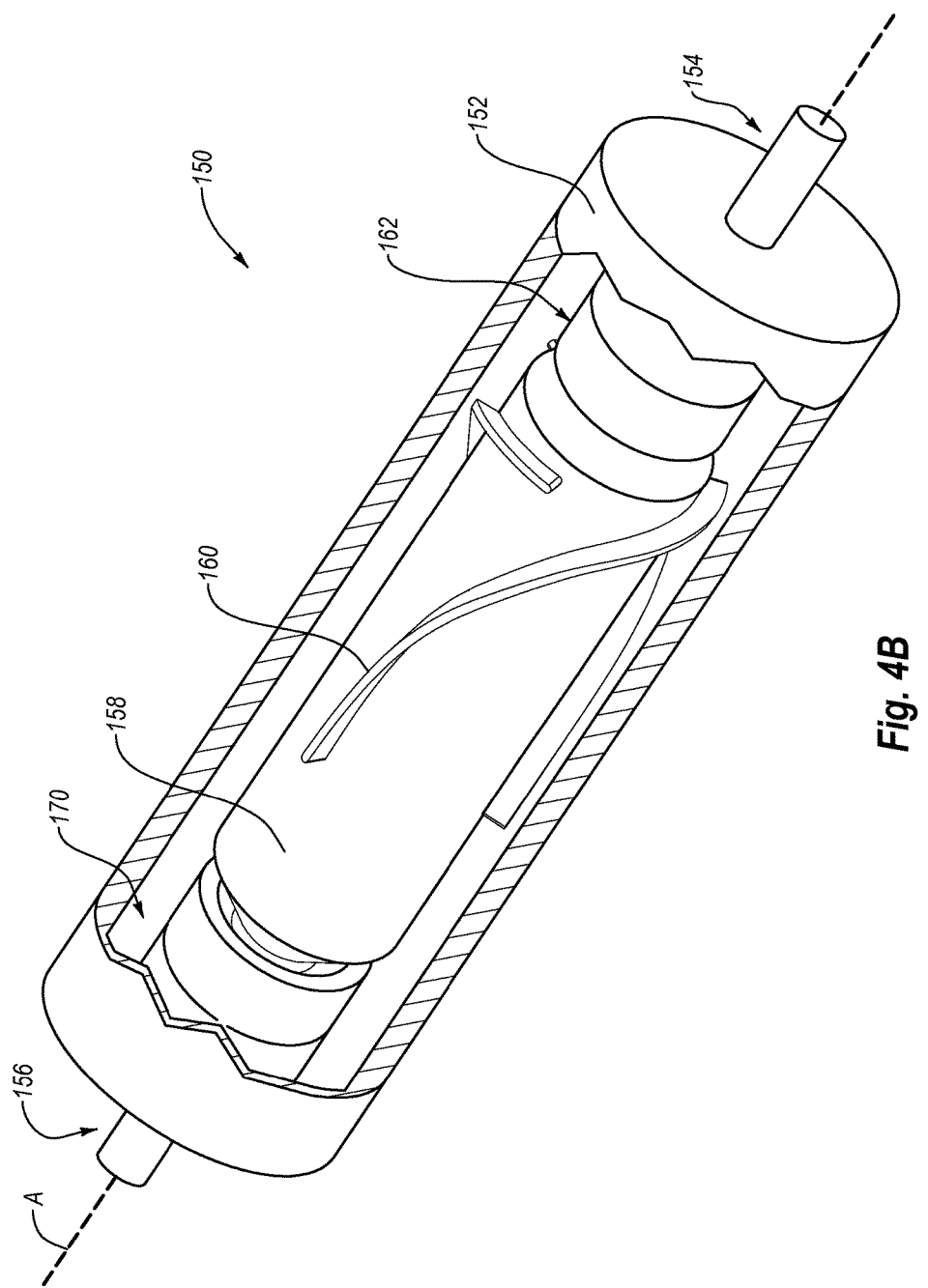
FIG. 4B is an isometric view of the axial-flow blood pump of FIG. 4A.

In an embodiment, the bearing assembly including rotor and stator components formed of PCD may be incorporated into a cardiopulmonary bypass blood pump. FIGS. 4A and 4B show an embodiment of such an axial-flow blood pump including PCD bearing components. As shown in FIG. 4A, a blood pump 150 may include a housing 152 including an inlet end 154, an outlet end 156, and a longitudinal axis A extending therebetween. A rotatable shaft 158 is disposed within housing 152 to be generally aligned with longitudinal axis A. Shaft 158 includes one or more impelling features (e.g., blades 160) on an exterior surface thereof positioned and configured to direct blood entering housing 152 through inlet end 154 towards outlet end 156.

The blood pump 150 further includes any suitable device for rotating rotatable shaft 158. Any suitable type of motor may be used. In one embodiment, the motor may be an electromagnetic motor. For example, the shaft may comprise a magnet material (e.g., neodymium or other rare earth magnetic material), while a power supply (not shown) provides power (e.g., direct current) to a motor within housing 152 to create the electromagnetic force needed to rotate shaft 158. The magnet material of shaft 158 may be disposed within the interior of shaft 158 so as to not be exposed to blood flow.

The blood contacting surfaces of the rotatable shaft and blades may be formed of a biocompatible metal material such as titanium, a cobalt-chromium alloy, or another biomedically acceptable material or alloy.

As seen in FIG. 4A, blood pump 150 includes an inlet bearing assembly 162 at an inlet end of rotatable shaft 158. Assembly 162 includes an inlet rotor 164 attached to the inlet end of shaft 158. Assembly 162 further includes an inlet stator 166 which receives a conical bearing surface 168 of inlet rotor 164. As shown, stator 166 may include a chamfered surface for contacting corresponding surface 168 of rotor 164. An opposite end of shaft 158 includes an outlet bearing assembly 170, which includes an outlet rotor 172 attached to the outlet end of shaft 158, which is received within outlet stator 174 in a similar manner as inlet bearing assembly 162.

Although blood pump 150 is shown with generally conically shaped PCD rotors (both at the inlet end and outlet end) it will be apparent that alternative rotor designs that may not be generally conical may alternatively be employed in such a blood pump. For example, a generally cylindrical rotor bearing surface could be received within a concentric hollow cylindrical stator. Other configurations will also be apparent to those of skill in the art in light of the present disclosure.

Shaft 158 may be rotated by any suitable motor at a desired speed, depending on the flow of blood to be provided and subject to any limitations to reduce or prevent blood damage, cavitation, or other undesirable effects. For example, other miniaturized axial-flow blood pumps (e.g., the JARVIK 2000) rotate at about 8,000 to about 12,000 RPM (e.g., about 10,000 RPM). Of course, the JARVIK 2000 is intended to be implanted within the patient, and so is very small (having a volume of about 25 cc and a mass of about 90 g). Where the blood pump is not required to be implanted within the patient, but is intended for use during a cardiopulmonary bypass treatment (where the pump may be positioned next to the patient on an operating table), the dimensions of the pump components may be considerably larger, and it may rotate at a significantly lower rate while delivering a desired flow of blood (e.g., about 4 L/min. to about 7 L/min.).

In an embodiment, the bearing surfaces of each rotor and stator of bearing assemblies 162 and 170 are formed of PCD which was sintered using a carbonate catalyst rather than a metal, such as cobalt or nickel. As a result, the interstitial regions defined between bonded diamond grains are generally not occupied by cobalt or nickel, but any interstitial regions occupied by a catalyst and/or derivative thereof are occupied by a carbonate catalyst and/or its derivative.

More particularly, the interstitial regions are substantially free of cobalt and nickel. The interstitial regions may also be substantially free of iron. While a tiny amount of cobalt, nickel, or iron may be present in an embodiment where the diamond particles used to form the PCD element were synthesized using cobalt, nickel, or iron, because no cobalt, nickel, or iron is employed when sintering the diamond particles to form the PCD element, any concentration of such cobalt, nickel, or iron is relatively low. For example, levels of incidentally present cobalt, nickel, or iron may be less than 1000 ppm, less than about 500 ppm, less than about 300 ppm, or less than about 100 ppm. Where such levels of residual cobalt, nickel, or iron are present, they may further aid in catalyzing the sintering of diamond particles under HPHT conditions when forming the PCD element.

Figure 5:
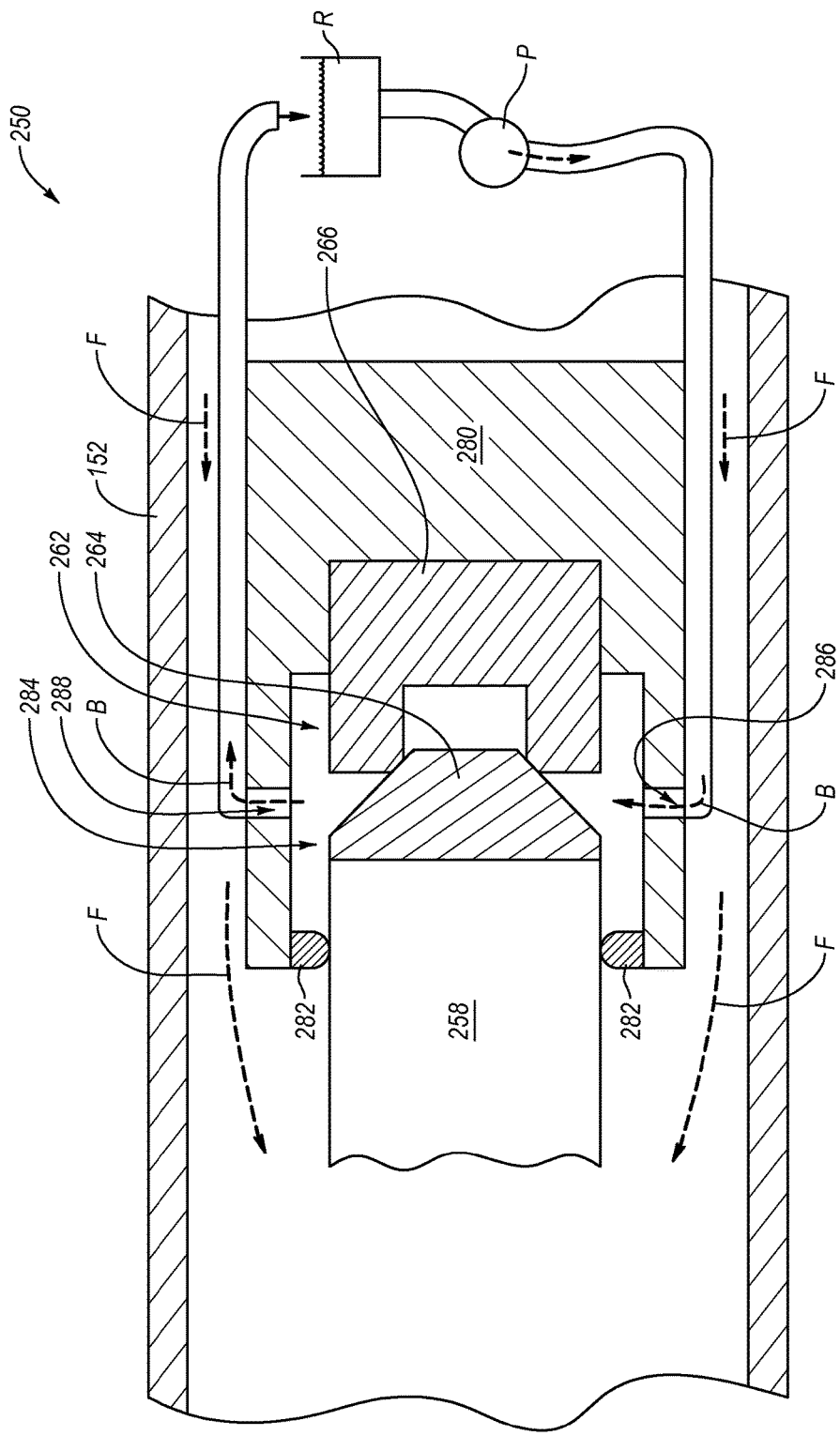
FIG. 5 is a schematic cross-sectional view of an embodiment of a PCD bearing assembly that is substantially sealed relative to the axial blood flow.

FIGS. 5-8 illustrate various additional sealed and unsealed bearing assembly configurations that may be employed in the inlet, outlet, or both bearing assemblies of the present axial flow blood pumps. FIG. 5 illustrates an inlet bearing assembly configuration in which bearing assembly 262 is at least substantially sealed from axial blood flow F. Bearing assembly 262 includes rotor 264 and stator 266, similar to that shown in FIG. 4A. The axial flow blood pump 250 may include a mounting member 280 to which stator 266 is mounted. An annular seal member 282 (e.g., an O-ring) provides a seal against rotatable shaft 258 to provide a substantially sealed bearing compartment 284, at least substantially preventing blood from axial blood flow F from entering compartment 284. Lubricating and/or cooling fluid B (e.g., water, oil, etc.) may be introduced into compartment 284 through bearing fluid inlet 286 and withdrawn through bearing fluid outlet 288. Fluid B may be cycled through reservoir R and pump P, and back into compartment 284 through inlet 286. As shown schematically, in an embodiment, blood flow F may be introduced through an inlet that directs blood flow F through an annular lumen that is concentric and coaxial with bearing fluid flow B. Other configurations may of course also be employed. Although the sealed bearing assembly configuration is shown at the inlet end of pump 250, it will be understood that a similar configuration may be provided at an outlet end of blood pump 250.

FIG. 6A also shows a sealed inlet bearing assembly configuration 262' of pump 250' similar to that shown in FIG. 5, but in which stator 266' and mounting member 280' are provided with a centrally disposed through passage 290 through which bearing fluid B may be introduced into sealed compartment 284. Bearing fluid B may be withdrawn from compartment 284 through one or more outlets 288, for recycling through reservoir R and pump P. As illustrated, rotor 264' may include one or more grooves 292, which may increase the turbulence of bearing fluid B within sealed compartment 284. Increased turbulence may increase the efficiency of cooling, lubrication, or both provided by bearing fluid B. FIGS. 6B and 6C illustrate end elevation views of rotor 264' and stator 266', respectively, showing grooves 292 and through passage 290, respectively.

A configuration similar to that shown in FIG. 6A may provide for a substantially sealed bearing assembly, but in which grooves 292 are omitted. Such a configuration may provide hydrodynamic performance of the bearing, where the surfaces are separated by a fluid film layer. For example, pump pressure may cause the bearing to ride on a fluid film layer. Hydrodynamic operation may decrease bearing wear and power losses (i.e., result in increased efficiency).

Figure 7:
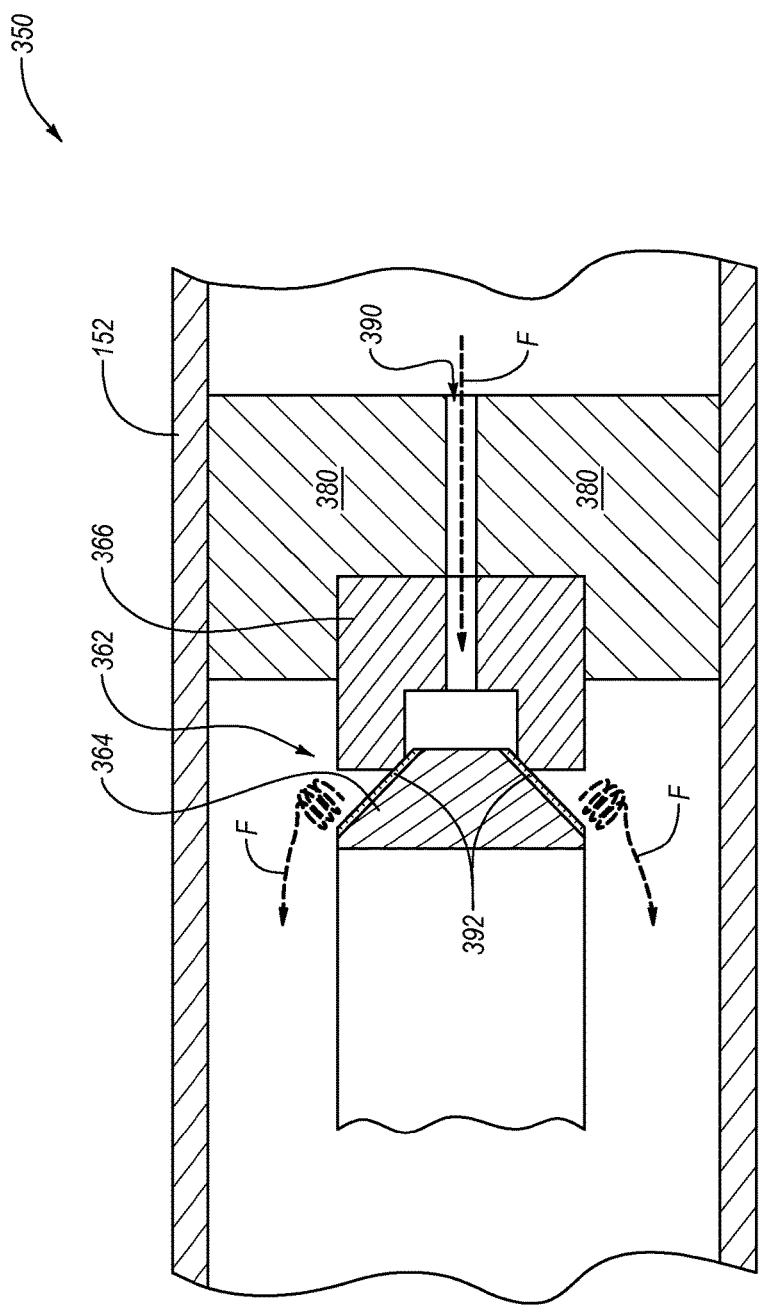
FIG. 7 is a cross-sectional view of an embodiment of an unsealed PCD bearing assembly that also includes a central through passageway in the stator and a plurality of grooves in a surface of the rotor.

FIG. 7 shows an unsealed inlet bearing assembly configuration 362 of pump 350 that is similar to that shown in FIG. 4A, except that stator 366 includes a through passage 390 and rotor 364 includes grooves 392. In addition, because stator 366 and mounting member 380 include through passage 390, at least a portion of blood flow F may be introduced into pump 350 through centrally disposed passage 390 where it may subsequently flow through grooves 392 of rotor 364. The rotation of grooves 392 may increase turbulent flow characteristics of blood flow F. As described above relative to FIG. 6A, hydrodynamic operation may be provided within a configuration similar to that shown in FIG. 7, but in which the grooves 392 are omitted.

Figure 8:
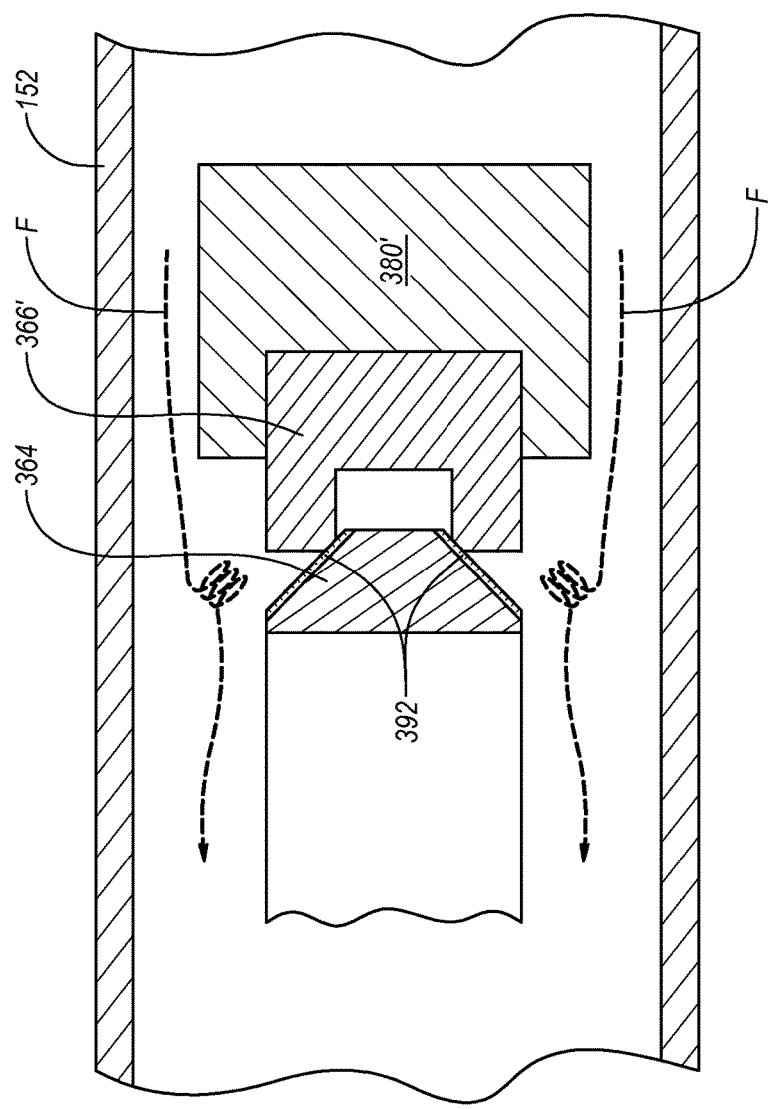
FIG. 8 is a cross-sectional view of an embodiment of an unsealed PCD bearing assembly that also includes a plurality of grooves in a surface of the rotor to induce turbulence in the axial blood flow.

FIG. 8 shows a configuration similar to that of FIG. 7, but in which no through passage is provided through mounting member 380' or stator 366'. As a result, blood flow F may be introduced in a configuration similar to that shown in FIG. 4A. Because rotor 364 includes grooves 392, increased turbulence may be imparted to blood flow F passing by grooves 392. Of course, any of the sealed or unsealed bearing assembly configurations (or others) may be employed at the inlet end, outlet end, or both of axial flow blood pumps as disclosed herein.

While various aspects and embodiments have been disclosed herein, other aspects and embodiments are contemplated. The various aspects and embodiments disclosed herein are for purposes of illustration and are not intended to be limiting. For example, while the use of PDCs formed using non-metallic catalysts is described, it will be understood that in embodiments where the PDC only contacts blood for a short period of time or not at all (e.g., sealed bearing assemblies) PDCs formed using traditionally employed catalysts such as cobalt, nickel, iron, or combinations thereof may be employed. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A bearing assembly for use within a cardiopulmonary bypass blood pump, the bearing assembly comprising:
   a bearing stator and a bearing rotor, each of the bearing stator and the bearing rotor including bearing surfaces that contact each other and/or form a fluid film layer therebetween during operation;
   each of the bearing stator and the bearing rotor including a polycrystalline diamond element having an associated bearing surface, each polycrystalline diamond element including a plurality of bonded diamond grains defining a plurality of interstitial regions therebetween;
wherein at least one of the plurality of interstitial regions include at least one of a non-metallic catalyst or at least one non-metallic catalyst derivative; or
substantially all of a catalyst material has been leached from the plurality of interstitial regions;
wherein the bearing stator at least partially defines a passageway configured to conduct fluid flow and the bearing surface thereof includes only a single bearing surface.

2. The bearing assembly of claim 1 wherein at least a portion of the bearing surface of the rotor exhibits a conically-shaped geometry.

3. The bearing assembly of claim 1 wherein the non-metallic catalyst or the at least one non-metallic catalyst derivative comprises at least one member selected from the group consisting of an alkali metal carbonate, an alkaline earth metal carbonate, and at least one derivative of the foregoing carbonates.

4. The bearing assembly of claim 1 wherein the non-metallic catalyst or the at least one non-metallic catalyst derivative comprises at least one of magnesium carbonate or at least one derivative of magnesium carbonate.

5. The bearing assembly of claim 1 wherein the at least one non-metallic catalyst derivative comprises an oxide.

6. The bearing assembly of claim 5 wherein the at least one non-metallic catalyst derivative comprises at least one of an alkali metal oxide or alkaline earth metal oxide.

7. The bearing assembly of claim 5 wherein the at least one non-metallic catalyst derivative comprises magnesium oxide.

8. The bearing assembly of claim 1 wherein a portion of the non-metallic catalyst or the at least one non-metallic catalyst derivative initially present upon formation of the bonded diamond grains within the plurality of interstitial regions has been leached from at least some of the plurality of interstitial regions.

9. The bearing assembly of claim 8 wherein substantially all of the non-metallic catalyst or the at least one non-metallic catalyst derivative initially present upon formation of the bonded diamond grains within the plurality of interstitial regions has been leached from at least some of the plurality of interstitial regions.

10. The bearing assembly of claim 1 wherein at least one of the bearing rotor or bearing stator comprises a tungsten carbide substrate to which the polycrystalline diamond element is bonded.

11. The bearing assembly of claim 1 wherein the bearing rotor or the bearing stator comprises a recess into which a portion of the corresponding bearing stator or bearing rotor is received, respectively.

12. The bearing assembly of claim 1 wherein the bearing surface of the bearing stator includes a inverted conically-shaped portion into which a conically-shaped portion of the bearing rotor is received.

13. The bearing assembly of claim 1 wherein the polycrystalline diamond element is substantially free of cobalt and nickel.

14. An axial-flow blood pump for use in cardiopulmonary bypass treatment, the axial-flow blood pump comprising:
a housing including an inlet at a first end and an outlet at a second end;
a rotatable shaft disposed within the housing between the inlet and the outlet, the rotatable shaft including an inlet end and an outlet end, the rotatable shaft including at least one blade on an exterior surface thereof configured to direct blood towards the outlet;
a motor configured to rotate the rotatable shaft about a longitudinal axis;
an inlet bearing assembly disposed at the inlet end of the rotatable shaft, the inlet bearing assembly including an inlet stator and an inlet rotor;
an outlet bearing assembly disposed at the outlet end of the rotatable shaft, the outlet bearing assembly including an outlet stator and an outlet rotor;
wherein each of the inlet stator, inlet rotor, outlet stator, and outlet rotor includes a polycrystalline diamond element including a bearing surface, wherein the bearing surface of the inlet stator and the bearing surface of the inlet rotor contact each other and/or form a first fluid film layer therebetween duration operation, wherein the bearing surface of the outlet stator is opposed to the bearing surface of the outlet rotor contact each other and/or form a second fluid film layer therebetween duration operation,
wherein at least one of the inlet stator or the outlet stator at least partially defines a passageway configured to conduct fluid flow and the bearing surface thereof includes only a single bearing surface; and
wherein each of the polycrystalline diamond elements comprises a plurality of bonded diamond grains defining a plurality of interstitial regions therebetween, wherein at least one of:
the plurality of interstitial regions include at least one of a non-metallic catalyst or at least one non-metallic catalyst derivative; or
substantially all of a catalyst material has been leached from the plurality of interstitial regions.

15. The axial-flow blood pump of claim 14 wherein the motor configured to rotate the rotatable shaft comprises an electromagnetic motor.

16. The axial-flow blood pump of claim 14 wherein at least a portion of the bearing surface of each of the inlet and outlet rotors exhibits a conically-shaped geometry.

17. The axial-flow blood pump of claim 14 wherein the bearing surface of at least one of the inlet stator or outlet stator comprises a inverted conically-shaped portion into which the conically-shaped portion of the inlet or outlet rotor is received.

18. The axial-flow blood pump of claim 14 wherein the non-metallic catalyst or the at least one non-metallic catalyst derivative comprises at least one member selected from the group consisting of an alkali metal carbonate, an alkaline earth metal carbonate, and at least one derivative of the foregoing carbonates.

19. The axial-flow blood pump of claim 14 wherein the non-metallic catalyst or the at least one non-metallic catalyst derivative comprises at least one of magnesium carbonate or at least one derivative of magnesium carbonate.

20. The axial-flow blood pump of claim 14 wherein the at least one non-metallic catalyst derivative comprises an oxide.

21. The axial-flow blood pump of claim 20 wherein the at least one non-metallic catalyst derivative comprises magnesium oxide.

22. The axial-flow blood pump of claim 14 wherein the polycrystalline diamond element is substantially free of cobalt and nickel.

23. An axial-flow blood pump for use in cardiopulmonary bypass treatment, the axial-flow blood pump comprising:

a housing including an inlet at a first end, an outlet at a second end, and a longitudinal axis extending therebetween;

a rotatable shaft disposed within the housing between the inlet and the outlet, the rotatable shaft including an inlet end and an outlet end, the rotatable shaft including at least one blade on an exterior surface thereof configured to direct blood towards the outlet;

a motor operatively coupled to the rotatable shaft and configured to rotate the rotatable shaft about the longitudinal axis;

an inlet bearing assembly disposed at the inlet end of the rotatable shaft, the inlet bearing assembly including an inlet stator and an inlet rotor, each of the inlet stator and the inlet rotor including bearing surfaces opposed to one another, wherein at least a portion of the bearing surface of the inlet rotor exhibits a conically-shaped geometry;

an outlet bearing assembly disposed at the outlet end of the rotatable shaft, the outlet bearing assembly including an outlet stator and an outlet rotor, each of the outlet stator and the outlet rotor including bearing surfaces opposed to one another, wherein at least a portion of the bearing surface of the outlet rotor exhibits a conically-shaped geometry; and at least one annular seal member that seals against the rotatable shaft and seals a bearing compartment, the bearing compartment including one of the inlet bearing assembly or the outlet bearing assembly;

wherein each of the bearing surfaces of the inlet stator, inlet rotor, outlet stator, and outlet rotor includes polycrystalline diamond element comprising a plurality of bonded diamond grains defining a plurality of interstitial regions therebetween, wherein at least one of the plurality of interstitial regions include at least one of a nonmetallic catalyst or at least one non-metallic catalyst derivative; or substantially all of a catalyst material has been leached from the plurality of interstitial regions;

wherein at least one of:

at least one of the inlet rotor or the outlet rotor includes one or more grooves; or at least one of the inlet stator or the outlet stator at least partially defines a passageway configured to conduct fluid flow.

24. The axial-flow blood pump of claim 14, further comprising at least one annular seal member configured to seal against the rotatable shaft and seal a bearing compartment, the bearing compartment including one of the inlet bearing assembly or the outlet bearing assembly positioned therein.

25. The bearing assembly of claim 1 wherein the bearing rotor includes one or more grooves.

26. The axial-flow blood pump of claim 14, wherein at least one of the inlet rotor or the outlet rotor includes one or more grooves.

27. The bearing assembly of claim 1 wherein at least one of the bearing stator or the bearing rotor includes a side surface, a distal surface, and a bearing edge at an intersection between the side surface and the distal surface, the bearing edge forming the bearing surface of the at least one of the bearing stator or the bearing rotor.

* * * * *